United States Patent [19]
Reinherz et al.

[11] Patent Number: 5,830,754
[45] Date of Patent: *Nov. 3, 1998

[54] RECOMBINANT DNA-PRODUCED T11 AND FRAGMENTS THEREOF

[75] Inventors: Ellis Reinherz, Lincoln; Peter Sayre, Cambridge; Hsiu-Ching Chang, Cambridge; Neil Richardson, Needham Heights, all of Mass.

[73] Assignee: Dana-Farber Cancer Institute, Boston, Mass.

[*] Notice: The term of this patent shall not extend beyond the expiration date of Pat. No. 5,550,055.

[21] Appl. No.: 361,014

[22] Filed: Dec. 21, 1994

Related U.S. Application Data

[63] Continuation of Ser. No. 902,436, Jun. 18, 1992, abandoned, which is a continuation of Ser. No. 714,323, Jun. 11, 1991, abandoned, which is a continuation of Ser. No. 932,871, Nov. 18, 1986, abandoned, which is a continuation-in-part of Ser. No. 913,988, Oct. 1, 1986, abandoned, which is a continuation-in-part of Ser. No. 906,413, Sep. 11, 1986, abandoned.

[51] Int. Cl.$^6$ .............................. C12N 5/00; C12N 15/00; C07H 21/02; C07H 21/04
[52] U.S. Cl. .................... 435/325; 435/320.1; 536/23.1; 536/23.5; 935/9; 935/12; 935/60; 935/70
[58] Field of Search ...................... 536/23.5; 435/172.3; 935/240.2

[56] References Cited

PUBLICATIONS

Milanese et al., J. of Immunol., "Clonal analysis of B cell growth and differentiaion activities induced from T lymphocytes upon triggering of T3–Ti and T11 pathways", 135:1884–1890 (1985).

Rosenberg et al., N.E. J. of Med., "Observations on the systemic administration of autologous lymphokine–activated killer cells and recombinant inter–leukin–2 to patients with metastatic cancer", 313:1485–1492 (1985).

Young et al, Proc. Natl. Acad. Sci 80 pp.1194–8 (1983).

Meyer et al, Cell 36 pp. 879–906 (1984).

Journal of Immunology 129(6) pp. 2479–2485 (1982).

Journal of Immunology 136(11) pp. 4099–4105 (1986).

Rose et al, Cell 30 pp. 753–762 (1982).

Sewell et al, Proc. Natl. Acad. Sci. 83 pp. 8718–8722 (1986).

Sewell, W.A. et al., *BioChem. Soc. Trans.* 14:1009 (1986).

Leca, G. et al., *Scand. J. Immunol.* 23:535–544 (1986).

Sewell, W.A. et al., *Proc. Natl. Acad. Sci., USA* 83:8718–8722 (Nov. 1986).

Brown, M.H. et al., *Eur. J. Immunol.* 17:15–20 (1987).

Sayre, P.H. et al., *Proc. Natl. Acad. Sci., USA* 84:2941–2941 (1987).

European Search Report.

Palouos et al J. F. Immunology 129(6):2479, 1982.

Treyer et al. J. F. Immunology 136(11):4099, 1986.

Meuer et l Cell 36: 897, 1984.

Yuury et al PNAS 80:1194, 1983.

Rose et al Cell 30: 753, 1982.

*Primary Examiner*—Deborah Crouch
*Attorney, Agent, or Firm*—Hamilton,Brook,Smith & Reynolds, P.C.

[57] ABSTRACT

A cDNA sequence encoding human T11 or a fragment thereof which is capable of inhibiting T-lymphocyte activation.

8 Claims, 6 Drawing Sheets

Fig. 1

```
                                                                              -14
AAAAGAGGAA ACCAACCCCT AAG ATG AGC TTT CCA TGT AAA TTT GTA GCC AGC TTC
                                 MET Ser Phe Pro Cys Lys Phe Val Ala Ser Phe
                                 |___________________________________________

5
CTT CTG ATT TTC AAT GTT TCT TCC AAA GGT GCA GTC TCC AAA GAG ATT ACG AAT
Leu Leu Ile Phe Asn Val Ser Ser Lys Gly Ala Val Ser Lys Glu Ile Thr Asn
                                                 |___________________________
                                                        N-term 23
GCC TTG GAA ACC TGG GCC TTG GGT CAG GAC ATC AAC TTG GAC ATT CCT AGT
Ala Leu Glu Thr Trp Ala Leu Gly Gln Asp Ile Asn Leu Asp Ile Pro Ser 41
TTT CAA ATG AGT GAT GAT ATT GAC GAT ATA AAA TGG GAA ACT TCA GAC AAG
Phe Gln Met Ser Asp Asp Ile Asp Asp Ile Lys Trp Glu Thr Ser Asp Lys 59
AAA AAG ATT GCA CAA TTC AGA AAA GAG ACT TTC AAG CAT CTG AAG ACC TGG
Lys Lys Ile Ala Gln Phe Arg Lys Glu Thr Phe Lys His Leu Lys Thr Trp 77
TAT AAG CTA TTT AAA AAT GGA ACT CTG AAA ATT AAG CAT CTG AAG ACC GAT GAT
Tyr Lys Leu Phe Lys Asn Gly Thr Leu Lys Ile Lys His Leu Lys Thr Asp Asp 95
CAG GAT ATC TAC AAG GTA TCA ATA TAT GAT ACA AAA GGA AAA AAT GTG TTG GAA
Gln Asp Ile Tyr Lys Val Ser Ile Tyr Asp Thr Lys Gly Lys Asn Val Leu Glu 113
AAA ATA TTT GAT TTG AAG ATT CAA GAG AGG GTC TCA AAA CCA AAG TCC TGG
Lys Ile Phe Asp Leu Lys Ile Gln Glu Arg Val Ser Lys Pro Lys Ile Ser Trp Fig. 2A
```

```
                                                                              131
ACT TGT ATC AAC ACA ACC CTG TGT GAG GTA ATG AAT GGA ACT GAC CCC GAA
Thr Cys Ile Asn Thr Thr Leu Cys Glu Val Met Asn Gly Thr Asp Pro Glu
         443                 458                 473           488
                                                   └──►
                                                   CNBr

149
TTA AAC CTG TAT CAA GAT GGG AAA CAT CTA AAA CTT TCT CAG AGG GTC ATC ACA
Leu Asn Leu Tyr Gln Asp Gly Lys His Leu Lys Leu Ser Gln Arg Val Ile Thr
         503                 518                 533

167
CAC AAG TGG ACC ACC CTG AGT GCA AAA TTC AAG TGC ACA GCA GGG AAC AAA
His Lys Trp Thr Thr Leu Ser Ala Lys Phe Lys Cys Thr Ala Gly Asn Lys
         548                 563                 578           593

185
GTC AGC AAG GAA TCC AGT GTC GAG CCT GTC AGC TGT CCA GAG AAA GGT CTG GAC
Val Ser Lys Glu Ser Ser Val Glu Pro Val Ser Cys Pro Glu Lys Gly Leu Asp
         608                 623                 638

203
ATC TAT CTC ATC ATT GGC ATA TGT GGA GGA GGC AGC CTC TTG ATG GTC TTT GTG
Ile Tyr Leu Ile Ile Gly Ile Cys Gly Gly Gly Ser Leu Leu Met Val Phe Val
         653                 668                 683           698
         ══════════════════════════════════════════════════════════════

221
GCA CTG CTC GTT TTC TAT ATC ACC AAA AGG AAA AAA CAG AGG AGT CGG AGA AAT
Ala Leu Leu Val Phe Tyr Ile Thr Lys Arg Lys Lys Gln Arg Ser Arg Arg Asn
         713                 728                 743           758
═════════════════════════

239
GAT GAG GAG CTG GAG ACA AGA GCC CAC AGA GTA GCT ACT GAA GAA AGG GGC CGG
Asp Glu Glu Leu Glu Thr Arg Ala His Arg Val Ala Thr Glu Glu Arg Gly Arg
         773                 788                 803

Fig. 2B
```

```
                                                     818                833                848                863
                                                 AAG CCC CAC CAA ATT CCA GCT TCA ACC CCT CAG AAT CCA GCA ACT TCC CAA CAT     257
                                                 Lys Pro His Gln Ile Pro Ala Ser Thr Pro Gln Asn Pro Ala Thr Ser Gln His
                                                         878                893                908
                                                 CCT CCA CCA CCT GGT CAT CGT TCC CAG GCA CCT AGT CAT CGT CCC CCG CCT         275
                                                 Pro Pro Pro Pro Gly His Arg Ser Gln Ala Pro Ser His Arg Pro Pro Pro
                                                     923                938                953                968
                                                 CCT GGA CAC CAG CGT GTT CAG CAC CAG CCT CAG AAG AGG CCT CCT GCT CCG TCG GGC 293
                                                 Pro Gly His Gln Arg Val Gln His Gln Pro Gln Lys Arg Pro Pro Ala Pro Ser Gly
                                                             983                998               1013               1028
                                                 ACA CAA GTT CAC CAG CAG AAA GGC CCG CCC CTC CCC AGA CCT CGA GTT CAG CCA     311
                                                 Thr Gln Val His Gln Gln Lys Gly Pro Pro Leu Pro Arg Pro Arg Val Gln Pro
                                                         1043              1058              1073                    1089
                                                 AAA CCT CCC CAT GGG GCA GCA GAA AAC TCA TTG TCC CCT TCC TCT AAT TAA AAAAGATAGA 327
                                                 Lys Pro Pro His Gly Ala Ala Glu Asn Ser Leu Ser Pro Ser Ser Asn ***
```

```
    1099      1109      1119      1129      1139      1149      1159
AACTGTCTTT TTCAATAAAA AGCACTGTGG ATTTCTGCCC TCCTGATGTG CATATCCGTA CTTCCATGAG
                                          ▲
    1169      1179      1189      1199      1209      1219      1229
GTGTTTTCTG TGTGCAGAAC ATTGTCACCT CCTGAGGCTG TGGGCCACAG CCACCTCTGC ATCTTCGAAC 1239      1249      1259      1269      1279      1289      1299
TCAGCCATGT GGTCAACATC TGGAGTTTTT GGTCTCCTCA GAGAGCTCCA TCACACCAGT AAGGAGAAGC 1309      1319      1329      1339      1349      1359      1369
AATATAAGTG TGATTGCAAG AATGGTAGAG GACCGAGCAC AGAAATCTTA GAGATTTCTT GTCCCCTCTC
```

Fig. 2C

```
      1379            1389       1399       1409       1419       1429       1439
AGGTCATGTG TAGATGCGAT AAATCAAGTG ATTGGTGTGC CTGGGTCTCA CTACAAGCAG CCTATCTGCT 1449            1459       1469       1479       1489       1499       1509
TAAGAGACTC TGGAGTTTCT TATGTGCCCT GGTGGACACT TGCCCACCAT CCTGTGAGTA AAAGTGAAAT

1519
AAAAGCTTTG ACTAGA
```

RECOMBINANT DNA-PRODUCED T11 AND FRAGMENTS THEREOF

This application is a continuation of application Ser. No. 07/902,436 filed Jun. 18, 1992, now abandoned, which is a continuation of Ser. No. 07/714,323 filed Jun. 11, 1991 (abandoned), which is a continuation of Ser. No. 06/932,871, filed Nov. 18, 1986 (abandoned), which is a continuation-in-part of Ser. No. 06/913,988, filed Oct. 1, 1986 (abandoned), which is a continuation-in-part of Ser. No. 06/906,413, filed Sep. 11, 1986 (abandoned).

BACKGROUND OF THE INVENTION

The work described herein was made with the aid of government funding, and the government therefore has certain rights in the invention.

This invention relates to human T-lymphocytes ("T-cells").

The T11 sheep erythrocyte binding glycoprotein [relative molecular mass ($M_r$) 50,000–55,000] is expressed throughout human T-lymphocyte ontogeny and appears to play an important physiological role in T-cell activation. The treatment of T cells with certain monoclonal anti-T11 antibodies results in antigen independent polyclonal T-cell activation as assessed by proliferation and lymphokine secretion. In addition, the majority of thymocytes that have not yet acquired the T3-Ti antigen/major histocompatibility complex (MHC) receptor can be activated to express interleukin-2 (IL-2) receptors through this T11 structure.

Three distinct epitopes on the 50K T11 molecule have been identified. While the $T11_1$ and $T11_2$ epitopes are expressed on resting as well as activated T cells, anti-$T11_3$ antibodies recognize a spatially distinct epitope that is preferentially expressed on mitogen- or antigen-activated T lymphocytes and thymocytes. The $T11_3$ epitope appears to represent a conformational change since it can be induced on resting T cells within 30 min at 4° C. by treatment with anti-$T11_2$. These studies have also shown that the combination of anti-$T11_2$ and anti-$T11_3$ (and to a lesser extent certain anti-$T11_1$ and anti-$T11_3$ antibodies) can induce IL-1-independent polyclonal T-cell activation as measured by proliferation and lymphokine secretion.

SUMMARY OF THE INVENTION

We have succeeded in producing a cDNA sequence encoding the human T11 molecule. In addition, we have completely sequenced the T11 cDNA, and thus know the deduced amino acid sequence of the T11 protein. We have inserted the T11 cDNA into an expression vector, which was used to transfect mammalian cells, which have been shown to express immunologically functional T11.

The deduced amino acid sequence of T11 has allowed us to identify the functional domains of the T11 molecule, which include the signal peptide, the external domain, the transmembrane anchor, and the internal cytoplasmic domain. Because it is the external domain which is recognized by and binds to the natural ligand of T11 found on human lymphocytes, truncated T11 can be produced by recombinant cells according to the invention, in which truncated T11 will be secreted by transfected cells for isolation and use in therapeutic applications which depend on the ability of the external domain of T11 to bind to its ligand, as will be explained in more detail below. The preferred genetic constructions thus are those encoding a human lymphocyte activation inhibiting fragment of T11, from which is deleted the transmembrane anchor and the cytoplasmic domain. Such fragments generally will bind to human lymphocytes and human red blood cells which express a homologous set of surface structures. A human lymphocyte inhibiting fragment is, as defined herein, a fragment which is capable of competing with the naturally-present T11 on the surface of a human lymphocyte, thus interfering with the ability of the lymphocyte to make contact with its target cells (if the lymphocyte is a cytolytic cell), or with macrophages having T11 binding structures which permit the cell-to-cell contact necessary for lymphocyte proliferation. To test a fragment for the ability to inhibit lymphocyte proliferation, or the cytotoxic effector function, the fragment is contacted with the lymphocytes prior to stimulation with mitogen, and the degree of proliferation is measured, using standard techniques, and the result is compared to a control in which the fragment was not used.

Other features and advantages of the invention will be apparent from the following description of the preferred embodiments thereof, and from the claims.

DESCRIPTION OF THE PREFERRED EMBODIMENTS

The drawings will first be described.

PURIFICATION AND CHARACTERIZATION OF T11

$4 \times 10^{10}$ Jurkat cells were washed twice in serum-free medium and lysed for one hour at 4° C. in 420 ml of 10 mM Tris, (pH 8.0) containing 0.15M NaCl, 1% vol/vol Triton-X-100 1 mM iodoacetamide and the following protease inhibitors (Sigma): phenylmethylsulfonylfluoride 1 mM, chymostatin (0.5 μg/ml), pepstatin (0.5 μg/ml), antipain (0.5 μg/ml), leupeptin (0.5 μg/ml), trypsin inhibitor (0.02 μg/ml). The crude lysate was centrifuged at 3000×g for 20 min. The supernatant was made 0.5% in sodium deoxycholate and ultra-centrifuged for 60 min at 150,000×g. $25 \times 10^6$ Jurkat cells from the same culture were surface radiolabelled by lactoperoxidase-catalyzed iodination. $2 \times 10^7$ radiolabelled cells were treated with 0.5 ml of lysis buffer and added to the large scale lysate. The combined lysates were applied at 0.75 ml/min to a 15 ml "pre-clear" column containing irrelevant mouse monoclonal antibodies anti-T3 (8C8), anti-$Ti_3$ (9H5) and anti-β2 microglobulin coupled to protein A Sepharose beads CL-4B (Pharmacia) at 5 mg antibody per ml of beads, followed by a 5 ml specific antibody column containing anti-$T11_1$ (8B5) coupled to protein A Sepharose at 5 mg/ml. The anti-T11 column was washed with 10 mM Tris, pH 8.0 with or without detergents and eluted in 1 ml fractions with 0.1 MM glycine, pH 3.0, 0.5% Triton-X 100. The fractions were collected in tubes containing 60 μl M Tris pH 8.0.

Fractions containing radioactivity were pooled, made 10% in glycerol and 2% in sodium dodecyl sulfate (SDS), heated at 60° C. for 20 min, loaded onto a 10% preparative polyacrylamide gel in a single lane 10 cm wide, and electrophoresed for 16 h at 40 volts. A 0.5 cm wide strip of the gel was dried and autoradiographed and the rest stained with Coomassie blue. Stained bands containing T11 were localized by comparison with the migration of surface labelled T11 as shown by the autoradiographed strip. Three regions of the gel at approximately 55, 53 and 50KD$_2$ were excised. Gel slices were washed with H$_2$O and electroeluted in 50mM ammonium bicarbonate containing 0.1% SDS for 16 h at 50 volts (Hunkapiller et al. Methods Enzymol. 91:227–236, 1983). Sample eluates were collected and proteins precipitated at –20° C. for 16 h by the addition of 9 volumes of cold ethanol. Precipitated proteins were collected by centrifugation and the protein pellets vacuum dried.

The ethanol precipitates were resuspended in 0.1% SDS and proteins were sequenced by Edman degradation on a gas phase protein sequenator (Applied Biosystems, model 120A) using the 03RPTH program and aqueous trifluoroacetic acid conversion chemistry. The PTH amino acids were identified with an on-line PTH analyzer (Applied Biosystems, model 120A) using a narrow-bore C18 reverse phase column run in acetate buffered 5% aqueous tetrahydrofuran and developed with acetonitrile. 5–10 μg from the 55, 53 and 50 KD$_2$ bands were analyzed and an identical N-terminal sequence was obtained for each. Eighteen of the 19 N-terminal positions were assigned as follows:

```
       1              10             18
       K E I T N A L E T X X X G A L G Q D I N
```

Isolation of cDNA Clones

A cDNA library was constructed as follows. RNA was isolated from the T4 helper clone 5B by the method of Chirgwin et al. (1979). Polyadenylated RNA was isolated by oligo(dT)-cellulose chromatography (Pharmacia PL type 7). cDNA was cloned into the expression vector pCDVI (Okayama & Berg Mol. Cell. Biol. 3:280–289, 1983). The vector was purchased from Pharmacia and the library constructed according to the manufacturer's protocol.

The 5B library was plated at 5–7x10$^3$ colonies per 150 mm diameter plate. Replicas were made onto GeneScreen Plus (NEN), amplified with chloramphenicol at 150 μg/ml, denatured, neutralized, washed, dried, and hybridized with redundant oligonucleotide probes. The above amino acid sequence information was used to design these anti-sense oligonucleotide probes:

Since a fully redundant set of 20mers matching the first seven amino acids would contain 792 different sequences, we synthesized four independent pools, each containing a redundancy of 196. A 48 redundant 14mer corresponding to the N-terminal residues 14–18 was also synthesized. Probes were synthesized using cyanoethyl phosphoramidites on an Applied Biosystems model 381A DNA synthesizer. After cleavage from the controlled pore glass column with NH$_4$OH, they were purified by passage over Sep-Pak C18 column (Millipore) and electrophoresis in 20% polyacrylamide gels.

Purified redundant oligonucleotide probes were end-labelled with T4 polynucleotide kinase (Bethesda Research Labs) using 200 μCi [α$^{32}$P]-ATP (Amersham) for 0.2 μg of oligonucleotide. Amplified filters were hybridized with 192 redundant 20mers at 40 C. in plaque screen buffer (50 mM Tris, pH 7.5, 1M NaCl, 1% SDS, 0.1% sodium pyrophosphate, 0.2% BSA, 0.2% Ficoll 400, 0.2% Polyvinyl pyrrahdone) for 16 h and washed at 43 C. in plaque screen salt (50mM Tris pH 7.5, 1M NaCl, 1% SDS, 0.2% sodium pyrophosphate) for 30 min. Colonies positive in the first round of screening were picked, replica plated, and rescreened with the 20mer. Identical replicas were also hybridized with the 48-redundant 14mer at 28 C. and washed at 31 C. The 20mers were used to screen the cDNA library. One pool of 20mers with a redundancy of 196 which hybridized in Northern analysis to T cell specific mRNAs identified 32 clones. These were isolated and rescreened with the 14mer. Seventeen of 32 clones contained sequences complementary to both probes. BamH I digests of plasmid DNA from these clones revealed that 11 contained 1.6Kb inserts, three contained 1.3Kb inserts, and that three clones had lost a BamH I restriction site. A representative 1.6Kb insert from a clone termed PB1 and a representative 1.3Kb insert from a clone termed PB2 were subcloned into the M13 vector mp18 (New England Biolabs) for sequencing by the dideoxy chain termination method. Primers were either the universal primers supplied by the manufacturer or 17mers synthesized on an Applied Biosystems model 381A.

10 μg of 5B RNA and poly(A)+ RNA from many cell types were electrophoresed under denaturing conditions in 7% formaldehyde and 0.02M NaPO$_4$, pH 7.0. The RNA was transferred to nitrocellulose and hybridized to $^{32}$P-labeled PB1 DNA in 50% formamide, 5X Denhardt's, 5X SSC, 0.1% SDS and 250 mμg/ml salmon sperm DNA for 12 h at 42 C. The probe was added at 2x10$^6$ cpm/ml. The filter was washed in 2xSSC, 0.1% SDS at 25 C. for 20 min and in 0.1% SSC, 0.1% SDS at 50 C. for 30 min and exposed to film for 48 h with an intensifying screen. In these experiments, PB1 DNA was labelled by random priming as described (Feinberg et al., 1983 Anal. Biochem. 132:6–13).

DNA T cell line from REX was restriction digested and electrophoresed in a 0.8% agarose gel. The gel was denatured, neutralized and transferred to nitrocellulose using 10 X SSC. Hybridization and washing procedures were as for northern analysis.

Figure 1:
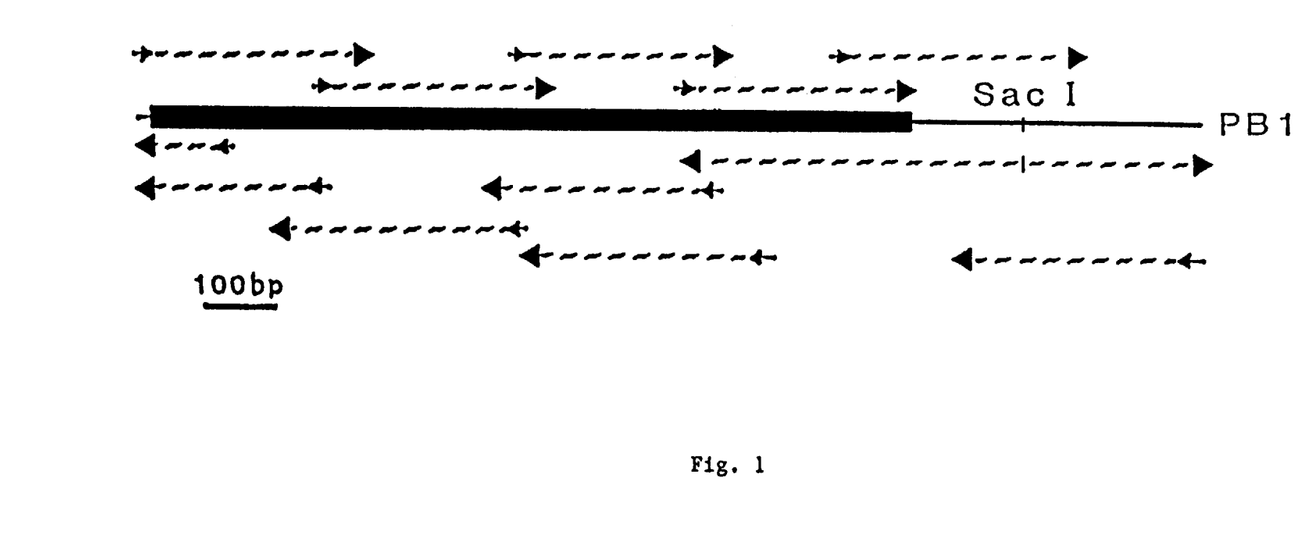
FIG. 1 is a diagrammatic representation of the strategy used in sequencing the cDNA (PB1) encoding T11.
Figure 2A:
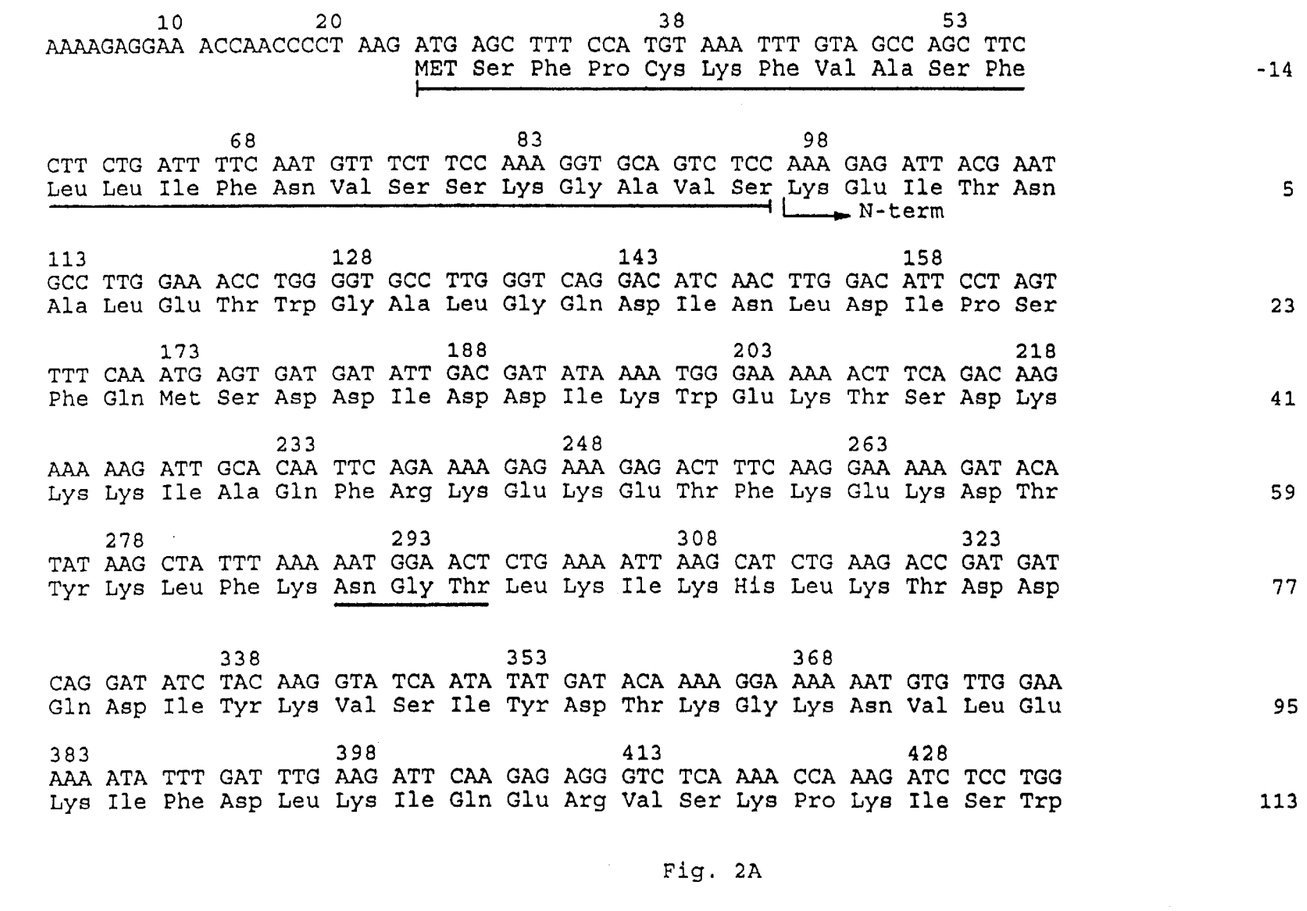
FIG. 2A–2D is the sequence of the PB1 cDNA, with the deduced amino acid sequence of T11 given on the bottom line.
Figure 2B:
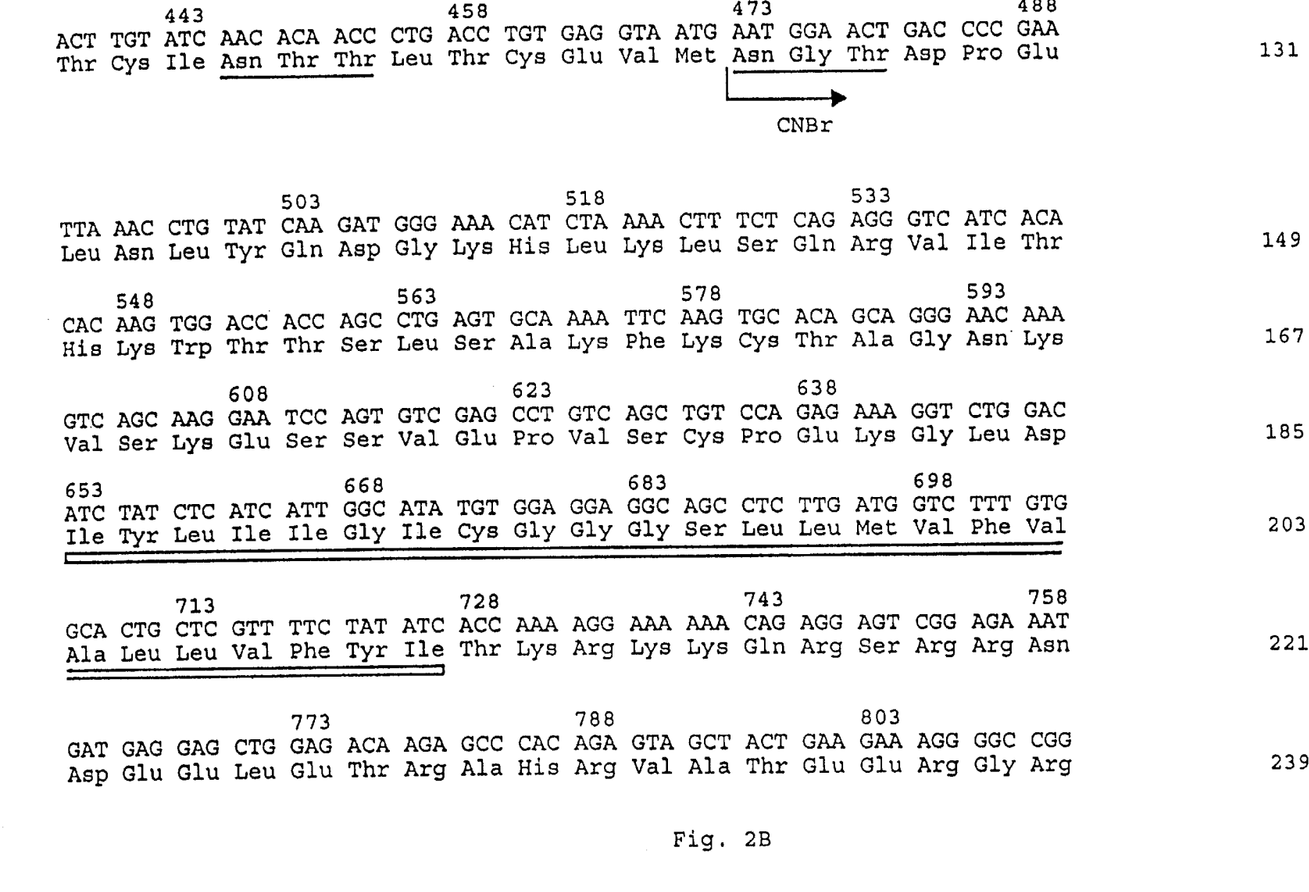
Figure 2C:
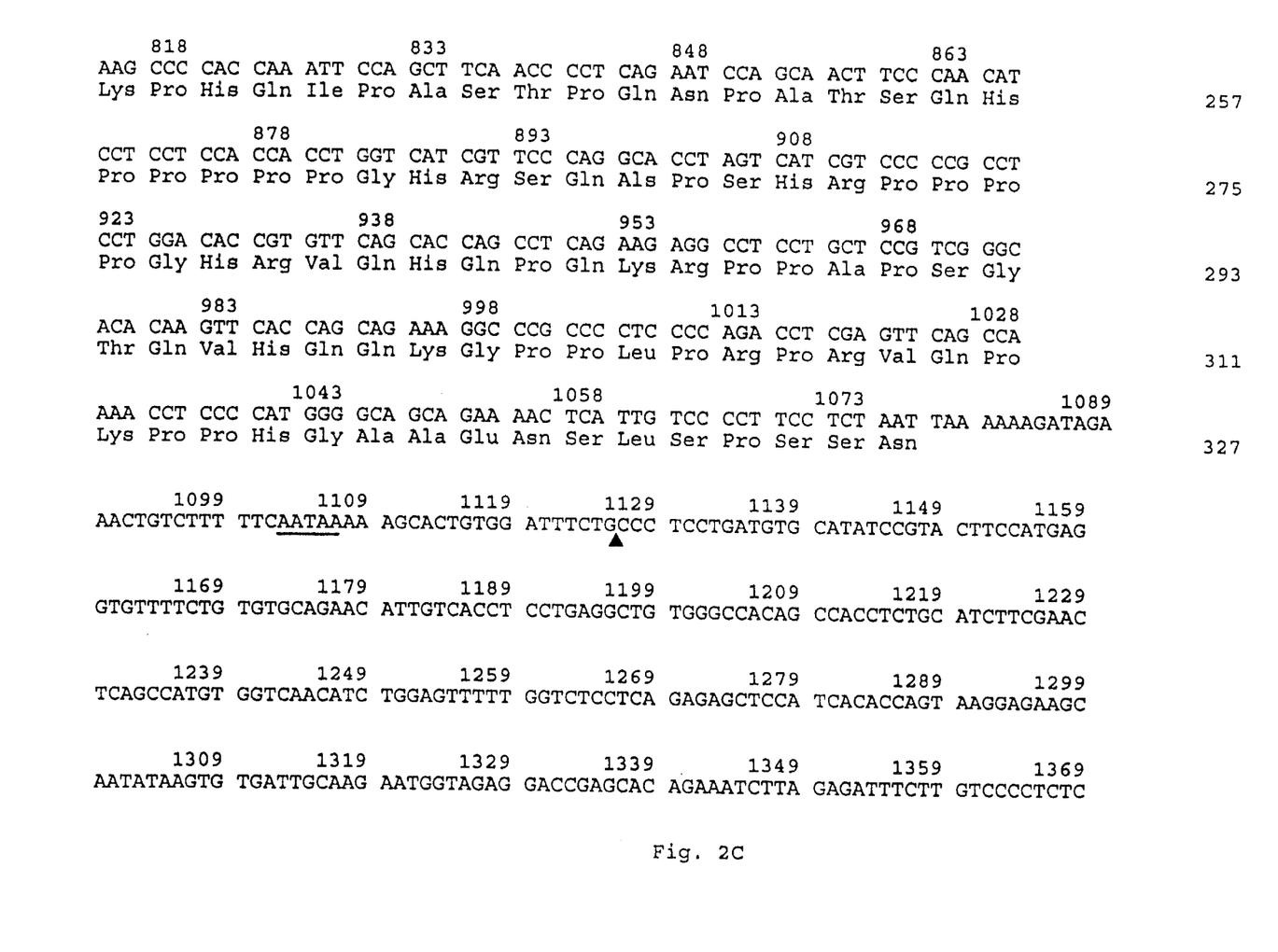
Figure 2D:
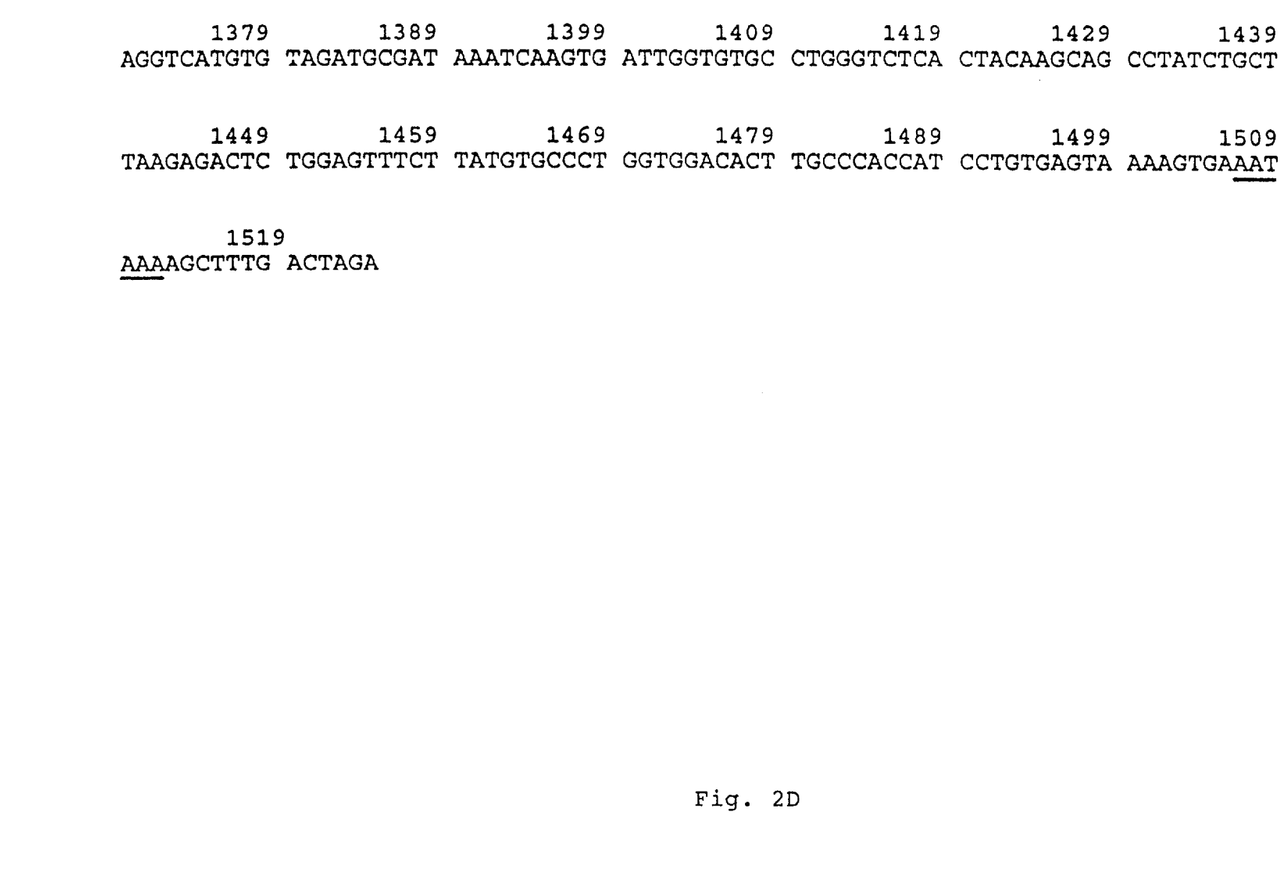

Referring to FIG. 1, the 1.6Kb insert of PB1 (solid line) was separated from the plasmid by BamHI digestion and subcloned into the M13 sequencing vector mp18. The M13 universal primer was used to derive initial sequence at the 5' end. Subsequently, primers of 17 nucleotides were used for dideoxy sequencing. Sequencing reactions were also performed on M13 clones which contained BamH I-Sac I and Sac I-BamH I fragments as shown. The open reading frame of the insert is identified by the thick solid bar.

Referring to FIG. 2A–2D, there is shown the cDNA and predicted protein sequence of PB1. The probable signal peptide (—), the NH$_2$-terminus of the mature protein (↪) and the position of a CNBr cleavage derived fragment (⇥) are shown. Polyadenylation signals at nucleotides 1103 and 1505 are underlined. The last nucleotide before the poly(A) tail in clone PB2 is indicated by an arrowhead at position 1126.

The complete nucleotide sequence of clone PB1 is 1,525 bases in length and flanked by a poly(A) sequence at its 3' end. An open reading frame of 1,053 bases (positions 24–1076) begins with an ATG methionine codon and is flanked by 23 nucleotides of 5' untranslated sequence and by 419 bases of 3' untranslated sequence. A polyadenylation signal (AATAAA) is located 18 bases upstream from the beginning of the poly(A) tail (FIG. 2). PB2 is identical to PB1 except that it lacks four nucleotides present at the 5' end of PB1 and has a shorter 3' untranslated region. A poly(A) tail was noted in PB2 after the nucleotide corresponding to residue 1126 in PB1 (arrow head). The bases from positions 1102 to 1103 form part of a Gln codon at amino acid 336 and a stop codon as well as the first five bases of the polyadenylation signal AATAAA (nucleotides 1102–1106) for mRNA corresponding to clone PB2.

The N-terminal lysine of the mature polypeptide is preceded by a sequence coding for a stretch of 24 hydrophobic amino acids which likely represents the signal sequence required for the T11 precursor to be transported across the endoplasmic reticulum. The cDNA sequence predicts three potential N-linked glycosylation sites (Asn-X-Ser/Thr) on the mature protein at amino acid positions 65, 117 and 126. An extremely hydrophobic stretch of 25 amino acids characteristic in size and composition of a transmembrane domain is found at positions 186–210. This region is followed by seven basic amino acids within the next ten residues consistent with the notion that this is the start of the intracytoplasmic domain. 21% of residues in the region of amino acids 211–336 are prolines. This cDNA sequence predicts a molecular weight for the mature polypeptide backbone of 37,994 daltons.

To determine the molecular weight of the broad 50–55$KD_2$ band in the absence of N-linked sugars, surface labelled T11 was digested with endoglycosidase and analyzed by SDS-PAGE. After digestion with endoF, there is a loss of the 55$KD_2$ band and the appearance of a major component at approximately 40$KD_2$. These data suggest that the 55$KD_2$ protein exists as a 40$KD_2$ structure in the absence of any N-linked sugar moieties and is consistent with the above determined molecular weight of the protein. These results are consistent with the possibility that all three N-linked glycosylation sites may be utilized.

Two related T11 mRNA species

Northern analysis using poly(A)+RNA or cytoplasmic RNA from a variety of sources indicates that expression of the PB1 and PB2 sequences is T lineage specific and yields two common bands of 1.7 and 1.3Kb. Thus, each of six human T lineage cells tested including activated T helper clones, thymus derived tumors, normal thymocytes, activated T cells, and resting peripheral blood T lymphocytes expresses the 1.7 and 1.3Kb transcripts. In contrast, non-T lineage cells such as normal peripheral blood B cells and macrophages, an Epstein-Barr virus-transformed B lymphoblastoid line, Laz 509, and the non-lymphoid hematopoietic cell lines HL-60 and U937 lack both transcripts. Given the similarity in size differences between the PB1 and PB2 inserts (~400 bases) and the two species of mRNA, it is likely that PB1 and PB2 cDNAs correspond to the 1.7Kb and 1.3Kb transcripts, respectively. This is further supported by the finding that an oligonucleotide based on a sequence from the 3' untranslated region unique to PB1 selectively hybridizes in northern analysis to sequences in the 1.7Kb site region.

Considerable variability exists within the level of expression of the 1.7 and 1.3Kb transcripts among individual T lineage tumor cells and physiologic T cell populations. Also, activated T cells express >10 fold higher amounts than resting T lymphocytes. This result is consistent with data indicating that T11 surface expression increases from 20,000 to 200,000 copies per cell upon activation with mitogens or antigens during a six day period and suggests that this differential expression is at least in part transcriptionally regulated.

PB1 homologous sequences are also expressed in murine thymocytes. However, under the conditions of hybridization, only the 1.3Kb molecular weight species is detected in poly(A)+mRNA from BALB/cJ thymocytes. It is thus likely that the murine species lacks the second polyadenylation signal in the 3' untranslated region of a homologous gene. This result also suggests that a highly homologous T11-related structure exists on murine T lineage cells.

The T11 molecule is encoded by a single copy gene

To determine the number of T11 genes present in the human genome, southern analysis was performed with the $^{32}$P-labeled PB1 insert. The probe hybridizes to a set of bonds of approximately 8 and 7Kb in a BamH I digest of genomic DNA from T cell line REX, to a single band >14Kb in EcoR I restricted REX DNA, and to a set of 7.4, 6.0 and 0.7Kb fragments in Hind III digested REX DNA. Analysis of DNA from granuloctyes gave an identical pattern, indicating that T11 is in the human genome as a single copy gene and, unlike the T cell receptor alpha, beta and gamma genes or the B cell immunoglobulin heavy and light chain genes, does not rearrange in lymphoid cells.

PB1 and PB2 cDNAs encode a functional T11 protein

To further prove that the sequences contained in the PB1 and PB2 cDNA clones encode the T11 protein and are themselves necessary and sufficient for T11 surface expression, COS-1 cells were transfected with PB1 or PB2 plasmid cDNAs or the unrelated IL-3 cDNA. COS-1 cells were plated at $4 \times 10^4$ cells/cm$^2$ in 6 well plates in RPMI 1640 (Gibco), 10% fetal calf serum, 0.03% glutamine, 1% penicillin-streptomycin. Six ug of PB2 or IL-3 (a gift of Ken-ichi Arai, DNAX) plasmid DNA was added to 350 $\mu$l RPMI and vortexed. 350 $\mu$l of 800 $\mu$g/ml DEAE-Dextran in RPMI, 100 mM Tris, pH 7.4 was added to the plasmid solution and vortexed. This solution was added to one well of cells which were then incubated for 3 h in a 37 C. incubator. The medium was aspirated and the cells washed once with RPMI. Subsequently, 2.5 ml of RPMI containing 2% fetal calf serum, 0.03% glutamine, 1% penicillin streptomycin, 150 $\mu$M chloroquine was added to each well and the cells incubated at 37 C. for 3 h. The cells were washed twice with RPMI and after addition of fresh medium, incubated for 48 h at 33° C. in a humid atmosphere to assay for surface T11 expression. Ten thousand cells in each transfection group were analyzed by fluorescence activated cell sorting.

After 48–72 h, expression of surface T11 on the transfected cell was determined on the basis of anti-T11 monoclonal antibody reactivity measured by indirect immunofluorescence on an Epics V cell sorter and by rosette formation with sheep erythrocytes.

The non-transfected COS 1 cells failed to interact with anti-T11$_1$ antibody. In contrast, after transfection with PB2, >25% of COS-1 cells express readily detectable surface T11 molecules. An identical level of reactivity was also detected with an anti-T11$_2$ monoclonal antibody. Similar levels of anti-T11$_1$ and anti-T11$_2$ reactivity resulted from transfections using PB1.

To next determine whether the transfected and expressed PB1 and PB2 sequences could themselves endow COS-1 cells with the ability to form aggregates with SRBC, transfected cells were tested for SRBC binding capacity. Incubation of SRBC with COS-1 cells resulted in no rosette formation. In contrast, after transfection of COS-1 cells with PB2, SRBC rosetting was observed. The SRBC rosette forming capacity was detected in COS-1 cells transfected with either of the two PB cDNAs separately or together. While the SRBC rosette capacity was not inhibited by monoclonal antibodies directed against the T3 subunits of the T3-Ti antigen/MHC receptor complex, the anti-T11$_1$ monoclonal antibody completely abrogated E rosette formation. Collectively, the above data provide unequivocal proof that the PB1 and PB2 cDNA sequences each independently encode a functional T11 protein.

Functional Domains of T11

Figure 3:
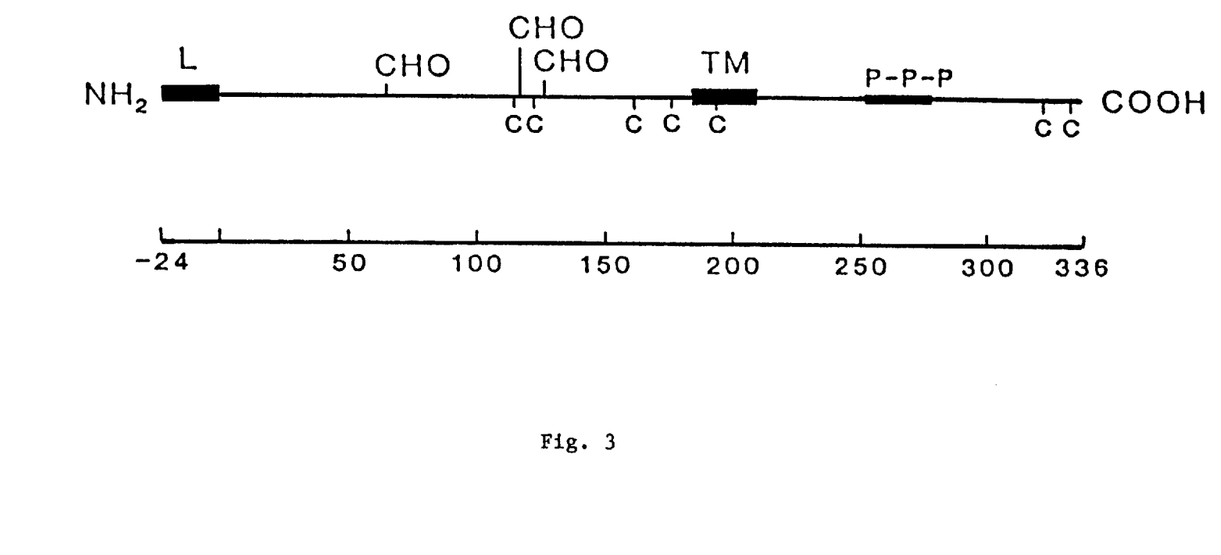
FIG. 3 is a diagrammatic representation of the T11 molecule, showing functional domains.

Referring to FIG. 3, the T11 molecule has a hydrophobic signal peptide (L), which is cleaved upon biosynthesis. The hydrophilic, 185 amino acid long external domain of the molecule is located outside the cell membrane. The hydrophobic 25 amino acid long transmembrane (TM) anchor region is embedded in the T-cell membrane, and the 126 amino acid long cytoplasmic domain of the molecule remains in the cytosol. In FIG. 3, the proline-rich region of this domain is indicated by P-P-P. The amino acid numbering corresponds to the mature peptide.

Cells transfected with PB1, like T-cells which naturally produce T11, do not secrete T11, but rather retain the T11 molecule by means of the transmembrane anchor, with only the external domain exposed. A truncated T11 molecule, with the transmembrane and cytoplasmic domains deleted, can, unlike the complete T11 molecule, be secreted by transfected cells and used in the applications described below. Such a truncated molecule can be prepared in a manner analogous to the method by which an anchor-minus IL-2 receptor molecule was prepared by Treiger et al. (1986) J. Immunol. 136, 4099. The truncated IL-2 receptor was found to be capable of binding to its ligand, IL-2.

To make the truncated T11 molecule, PB1 or PB2 cDNA representing the gene for the entire T11 molecule will be restricted with Pvu II. This enzyme uniquely cuts within the 1,525 base pair T11 molecule cDNA insert between bases 628 and 629, resulting in removal of all transmembrane and intracytoplasmic sequences and seven amino acids of the external domain. Subsequently, a 14 base phosphorylated synthetic oligonucleotide (CTAAGAATTCTTAG) containing the third base of the codon for amino acid 178, a termination codon TAA followed by the six base recognition sequence for EcoR I (GAATTC), and four nucleotides (TTAG) complementary to CTAA, will be ligated to the Pvu II restricted plasmid DNA with T4 DNA ligase. The DNA will then be digested with Pst I to separate the 5' end of the cDNA insert from the plasmid DNA and then subcloned into an appropriate expression vector. For example, this fragment could be blunted by T4 DNA polymerase to remove the Pst site and then be ligated to the EcoR I linker by T4 ligase. Finally, it could be digested with EcoR I before ligation into the unique EcoR I site of the publicly available pcEXV-1 expression vector.

Use of T11

The T11 protein, or its truncated, secreted form, can be used in a variety of diagnostic and therapeutic applications, all of which are based on the binding of T11 to its natural ligand on human lymphocytes and homologous surface structures present on target cells which facilitate T lymphocyte—target cell interactions, which result in target cell lysis or lymphocyte proliferation. (Siliciano et al. Nature 317:428–431 (1985); and Palacios and Martinez-Maza, J. Immunol. 129:2479–2485 (1982)).

The T11 molecule is expressed on the surface of many human T-cell malignancies, e.g., T-cell leukemias and lymphomas. In addition, autoimmune diseases, e.g., rheumatoid arthritis and systemic lupus erythmatosus (SLE), are characterized by the presence in the blood and lymph of large numbers of T11-bearing T-cells. Rapid cell turnover in these disease states can cause the shedding of the T11 molecule into the bloodstream.

T11 can be used as an immunogen to produce polyclonal or monoclonal anti-T11 antibodies, using conventional techniques. These antibodies can be labeled with any conventional label, e.g., radioisotopes, and used in conventional immunoassay methods to measure serum T11 levels and thus monitor patients having T-cell-associated diseases. Particularly sensitive ELISA-type assays will employ two anti-T11 antibodies, each to a different antigenic determinant on the surface of T11, in a sandwich format.

Another use for the anti-T11 antibodies is in the purification of recombinant T11, produced as described above. The anti-T11 is coupled to a column and T11-containing media is passed through the column so that the T11 reversibly binds to the T11, after which Anti-T11 antibodies is eluted in purified form, according to conventional methods.

The disease states which can be treated using T11 include medical conditions characterized by unwanted activity of the immune system which results in excess T-cell activation, which plays a key role in the amplification of the immune response. These conditions include rheumatoid arthritis; systemic lupus erythmatosus; juvenile onset diabetes; multiple sclerosis; allergic conditions; inflammatory conditions such as eczema, ulcerative colitis, inflammatory bowel disease, and Crohn's disease; and allograft rejection (e.g., rejection of a transplanted heart or kidney). Soluble T11 competes with the surface-bound T11 for its ligand on target cells thus dampening immune response amplification. The T11 admixed with a pharmaceutically acceptable carrier substance such as saline, is administered intravenously to a human patient in an effective amount, e.g., 20 $\mu$g to 500 $\mu$g per kg body weight. For some conditions, T11 can be administered directly to the site where needed most; for example, T11 can be injected directly into the inflamed joint of a human patient suffering from rhematoid arthritis.

DEPOSITS

Plasmid PB1 is were deposited on Oct. 1, 1986 in the American Type Culture Collection, Rockville, Md., and assigned ATCC Accession Number ATCC No. 40268; deposit date: Oct. 1, 1986.

Applicants' assignee, Dana-Farber Cancer Institute, acknowledges its responsibility to supply a sufficient quantity of the plasmid DNA for the term of a patent issued hereon, 5 years after the last request for the plasmid, or 30 years from the date of deposit, whichever is the longer, and its responsibility to notify the depository of the issuance of such a patent, at which time the deposits will be made irrevocably available to the public. Until that time the deposit will be made available to the Commissioner of Patents under the terms of 37 C.F.R. Section 1–14 and 35 U.S.C. Section 112.

Other embodiments are within the following claims.

We claim:

1. Isolated nucleic acid having a nucleotide sequence encoding the human T11 protein having the amino acid sequence set forth in FIG. 2A–2D.

2. A vector comprising DNA having a nucleotide sequence encoding the human T11 protein having the amino acid sequence set forth in FIG. 2A–2D.

3. A cell transformed with a vector comprising DNA having a nucleotide sequence encoding the human T11 protein having the amino acid sequence set forth in FIG. 2A–2D.

4. A cell transformed with a vector comprising DNA having a nucleotide sequence encoding the human T11 protein having the amino acid sequence set forth in FIG. 2A–2D, which cell is capable of expressing human T11 protein.

5. Nucleic acid having a nucleotide sequence which encodes a polypeptide having an amino acid sequence shown as amino acids −24 through 178 in FIG. 2A–2D.

6. A vector comprising nucleic acid having a nucleotide sequence encoding a protein having the amino acid sequence shown as amino acids −24 through 178 in FIG. 2A–2D.

7. A cell comprising a vector of claim 6.

8. The cell of claim 7, wherein said cell secretes a truncated human T11 protein.

* * * * *